(12) United States Patent
Sundberg et al.

(10) Patent No.: US 7,585,391 B2
(45) Date of Patent: Sep. 8, 2009

(54) PAPER SIZING COMPOSITION

(75) Inventors: Kenneth Sundberg, Abo (FI); John Roberts, Hyde (GB); Claes Zetter, Turku (FI); Guomei Peng, Clitheroe (GB)

(73) Assignee: Ciba Specialty Chemicals Corporation, Tarrytown, NY (US)

( * ) Notice: Subject to any disclaimer, the term of this patent is extended or adjusted under 35 U.S.C. 154(b) by 0 days.

(21) Appl. No.: 10/517,413

(22) PCT Filed: Jun. 12, 2003

(86) PCT No.: PCT/GB03/02534

§ 371 (c)(1),
(2), (4) Date: May 16, 2005

(87) PCT Pub. No.: WO03/106767

PCT Pub. Date: Dec. 24, 2003

(65) Prior Publication Data

US 2005/0224202 A1 Oct. 13, 2005

(30) Foreign Application Priority Data

Jun. 12, 2002 (GB) .................................. 0213424.5

(51) Int. Cl.
*D21H 21/16* (2006.01)
*C07D 307/60* (2006.01)
(52) U.S. Cl. .................... 162/158; 162/135; 549/233
(58) Field of Classification Search ............... 162/135, 162/158; 549/233
See application file for complete search history.

(56) References Cited

U.S. PATENT DOCUMENTS

| 3,412,111 | A | * | 11/1968 | Irwin et al. .................. 549/255 |
| 4,375,145 | A | * | 3/1983 | Mosse et al. ................... 53/425 |
| 4,559,103 | A | * | 12/1985 | Nomura et al. ............... 162/160 |
| 4,611,087 | A |   | 9/1986 | Yamashita et al. ............. 560/81 |
| 4,956,478 | A | * | 9/1990 | Fakoukakis et al. ......... 549/255 |
| 4,958,034 | A | * | 9/1990 | Hale et al. ................... 549/255 |
| 5,021,169 | A |   | 6/1991 | Shin et al. .................... 549/255 |
| 5,118,565 | A | * | 6/1992 | Suzuki ........................ 428/336 |
| 5,350,568 | A | * | 9/1994 | Tuckner et al. .............. 422/300 |
| 5,603,997 | A |   | 2/1997 | Lindgren et al. ........... 428/34.2 |
| 5,626,719 | A | * | 5/1997 | Tansley et al. .............. 162/158 |
| 5,939,562 | A |   | 8/1999 | Kapanen et al. ............. 549/255 |
| 5,969,011 | A | * | 10/1999 | Frolich et al. ................. 524/35 |
| 6,110,548 | A | * | 8/2000 | Kinsey ....................... 428/34.2 |
| 6,120,730 | A | * | 9/2000 | Palaniappan et al. .......... 422/28 |
| 6,359,093 | B1 |   | 3/2002 | Takaki et al. ............. 526/307.6 |
| 2006/0231223 | A1 | * | 10/2006 | Ward et al. ..................... 162/70 |

FOREIGN PATENT DOCUMENTS

| EP | 0359316 |   | 3/1990 |
| JP | 62106091 | A * | 5/1987 |
| WO | 97/30039 |   | 8/1997 |
| WO | 00/20686 |   | 4/2000 |

OTHER PUBLICATIONS

English Translation of JP 62106091 A, US Patent and Trademark Office Translations Branch.*
EPA publication 201-16228A, "Higher Alkenyl Succinic Anhydride (ASA) Category Justification and Test Plan," 2006, pp. 1 and 8-11 [online], [retrieved on Jun. 4, 2009], retrieved from the Internet <URL: http://www.epa.gov/hpv/pubs/summaries/hialksan/c16228tp.pdf>.*

* cited by examiner

*Primary Examiner*—Eric Hug
*Assistant Examiner*—Dennis Cordray
(74) *Attorney, Agent, or Firm*—Shiela A. Loggins

(57) ABSTRACT

The invention relates to the sizing of paper and board using alkenyl succinic anhydride (ASA). The invention provides a sizing composition which comprises an aqueous emulsion of an ASA wherein the ASA incorporates a maximum of 1% by weight (preferably a maximum of 0.5% by weight) of polymeric residues. The composition may incorporate less than 0.5% by weight of olefins. Paper sizing compositions in accordance with the invention provide enhanced resistance to penetration of the edges of paper and board by agents such as hot hydrogen peroxide and lactic acid.

13 Claims, No Drawings

PAPER SIZING COMPOSITION

This application is a 371 of PCT/GB03/02534, filed Jun. 12, 2003 which claims the benefit of British Application No. 0213424.5, filed Jun. 12, 2002.

The present invention relates to alkenyl succinic anhydride (ASA) and more particularly to its use in the sizing of paper and board.

Paper sizing may be effected using a number of different materials. For example, it is known to effect sizing using a rosin emulsion in conjunction with an aluminium salt (e.g. papermakers' alum) which is effective to cause deposition of the rosin onto the fibres being sized. It is also known to use reactive sizes (e.g. alkyl ketene dimer (AKD) and alkenyl succinic anhydride (ASA), the latter being more reactive than the former).

ASA is normally produced by the reaction of a mixture of long chain alkenes which are such that the olefinic double bond is otherwise than at the α position. The alkene mixture used for this reaction is, in turn, generally obtained by catalytic isomerisation of α-olefins. ASA is a product generally represented by the formula:

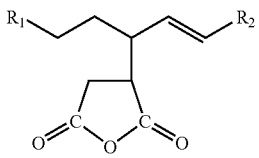

where $R_1$ and $R_2$ are the same or different alkyl chains.

The reaction of the alkenes with maleic anhydride is conducted with a molar excess of the olefins and is continued until almost zero maleic anhydride content. After the reaction, excess olefin is removed by distillation under reduced pressure (but at pressures which are not low enough to distil the ASA) and is recycled.

For use as a paper sizing agent, the ASA is generally formulated as an emulsion incorporating a stabiliser such as, for example, a starch, a cationic polyacrylamide or other cationic polymer. For use in paper sizing, the emulsion is added to the wet-end of a paper/board making process and may be added to the so-called thick stock (usually comprised of 2% to 5%, e.g. about 3%, by weight of paper making fibres) or to the thin stock (usually comprised of up to 1%, e.g. about 0.5%, by weight of the fibres). Alternatively the ASA emulsion may be added at the size press.

ASA emulsions are perfectly satisfactory for use in the production of paper and board intended for a wide variety of applications. However they are not currently used (to our knowledge) in the production of so-called "liquid packaging board" which is used for manufacturing cartons and the like for containing liquids, frequently a dairy product such as milk or cream. The liquid packaging board comprises the cellulosic board substrate which is coated on one or both sides thereof with a barrier preventing or inhibiting penetration of the substrate by the liquid to be contained in a carton or the like produced from the board. Frequently the barrier material is of polyethylene but other food grade materials may also be used.

Generally the board is sterilised for use in the production of a septic container. Such sterilisation may be effected after the board has been coated with the barrier material and cut to the required size. The sterilisation is generally effected by means of baths of hydrogen peroxide at elevated temperature. There is however the disadvantage that the hot hydrogen peroxide is able to "infiltrate" the board at its cut edges resulting in undesireable swelling of the fibres from which the board is formed.

It is an object of the present invention to obviate or mitigate the above mentioned disadvantages.

According to a first aspect of the present invention there is provided a paper sizing composition which comprises an aqueous emulsion of an ASA wherein the ASA incorporates a maximum of 1% by weight of polymeric residues.

According to a second aspect of the present invention there is provided a method of producing a sized paper or board wherein the sizing agent is an ASA incorporating a maximum of 1% by weight of polymeric residues.

Sized paper or board produced in accordance with the method of the second aspect of the invention may be used for food grade/catering applications. The board may be used, for example, for cartons intended to contain liquids such as milk, and cream. Alternatively the board may be used for producing paper cups or the like.

We have in fact found that the use of an ASA containing at most 1% of polymeric residues (as opposed to a "conventional" ASA which would normally contain 7-10% of such residues) as a sizing agent provides enhanced resistance to edge penetration by agents such as hot hydrogen peroxide and lactic acid. Thus paper or board which has been sized in accordance with the method of the second aspect of the invention may be provided with a barrier coating, e.g. polyethylene or other barrier material that has food contact approval, on both surfaces thereof and (after being cut to size if necessary) be sterilised in a bath of hot hydrogen peroxide prior to being converted to cartons of the like, particularly for containing dairy products.

The ASA employed in the present invention preferably contains less than 0.5% by weight of polymeric residues. Furthermore the ASA preferably contains less than 5%, more preferably less than 4% and even more preferably less than 3% by weight of olefins. In particularly preferred embodiments of the invention, the ASA contains less than 1%, more preferably less than 0.5% by weight of olefins.

The ASA employed in the present invention (i.e. one containing a maximum of 1% of polymeric residues) may be an ASA distillate. By the term "ASA distillate" we mean a product that has been obtained by distilling ASA in the sense that the ASA is converted to the vapour phase and subsequently re-condensed to give a distillate. The product to be distilled may be the reaction product of maleic anhydride with a mixture of olefins, most preferably after removal of unreacted olefins. In other words, the preferred product for distillation is the ASA that is normally used as the material for formulating an ASA sizing composition.

The ASA distillate will generally be obtained by an overall process which involves the steps of:

(i) reaction of a mixture of olefins with maleic anhydride;
(ii) removal of excess olefin by distillation under reduced pressure (but at pressures which are not low enough to distil the ASA); and
(iii) distillation of the product from step (ii) at sufficiently reduced pressure to "distill over" the ASA.

Steps (i) and (ii) are entirely conventional and are the steps used to produce ASA which is then formulated into paper sizing compositions. Thus, for example, a product resulting from steps (i) and (ii) is commercially available under the name RAISAFOB MF.

Distillation of the "crude" ASA to produce the ASA distillate will be conducted at elevated temperature and reduced pressure. Generally the pressure will be a maximum of 100 Pa (1 mbar) for which a distillation temperature of 200-210° C. is suitable. It is however more preferred that lower pressures are used, most preferably less than 0.5 Pa ($4\times10^{-3}$ mm Hg). At this pressure, the temperature at which distillation is conducted will generally be 140-160° C.

Distillation may be effected using a wiped film evaporator.

ASA distillates as employed in the present invention will generally contain less than 0.5% by weight of residual polymer content. In contrast the corresponding value for "undistilled" ASA is 7-9% by weight.

If it is desired that the ASA distillate has a low free olefin content then it will generally be necessary to take steps to prevent free olefin being incorporated in the condensate that is to be used for making the sizing emulsion. For example, when a wiped film evaporator is used for distillation then a volatiles trap may be employed.

ASA distillates have better colour the "conventional" ASA and may for example have a Gardner colour of about 2 as compared with the value of 4-11 for the undistilled product. Additionally the ASA distillates demonstrate improved size performance (both in terms of Cobb and HST (Hercules Size Test)). These advantages are, of course, additional to those of improved lactic acid resistance and peroxide resistance which have been mentioned earlier.

The ASA distillate may be formulated into a sizing composition, e.g. an emulsion, in exactly the same way as "conventional" ASA. Thus, the ASA distillate may be emulsified in water together with a starch stabiliser. It will generally also be, appropriate to use a stabiliser in the formation of the emulsion. Examples of suitable stabilisers are well known in the art and include, for example, starch, ionic starch including cationic and anionic starch, (e.g. potato or waxy maize starch) or a cationic polyacrylamide or other cationic polymer. The amount of stabiliser used is usually up to 25% by weight based on the weight of ASA, more preferably 5% to 20% on the same basis.

Optionally the emulsion will contain at least one surfactant. Examples of suitable surfactants are well known in the art and include, for example, phosphate, esters, phosphate ethers, nonyl phenol ethoxylates, polyacrylamides, and lignosulphonic acid derivatives. The amount of surfactant used is generally up to 5% by weight of ASA.

If desired, a metal cation may be incorporated with the ASA to be emulsified to provide an emulsion having a coating of an insoluble salt of alkenyl succinic acid in accordance with the teachings of WO-A-0020686 (Raisio).

The emulsion in accordance with the invention may be used in an entirely conventional means for sizing of fibres to be used for the formation of paper, board and like material. For this purpose, the emulsion will be added to the wet-end of a paper making process and may be added to the so-called thick stock (usually comprised of 2% to 5%, e.g. about 3%, by weight of the papermaking fibres) or to the thin stock (usually comprised of up to 1%, e.g. about 0.5% by weight of the papermaking fibres). Alternatively the ASA emulsion may be added at the size press.

The invention will now be further described with reference to the following Examples.

EXAMPLES

The Example illustrates distillations of a batch of Raisofob MF (Batch A) for which an analysis of olefin and polymeric residue content is given in Table 1 below together with the same analysis for other batches of Raisofob for the purposes of comparison.

1. ASA Distillation (i) Laboratory Distillation (Small Scale)

A conventional vacuum distillation system was used. Approximately 200 ml Raisafob MF (Batch A) were introduced into a 500 ml round bottomed flask filled with a distillation head and a simple air condenser. The flask was heated in an oil bath. The temperature and pressure conditions were 200-210° C. and 100 Pa (1.0 mbar). The first fraction, containing approximately 5% unreacted olefin was discarded.

(ii) Plant Distillation (Production Scale)

A Wiped Film Evaporator was used to distil 2 tonnes of Raisafob MF (Batch A).

The wiped film evaporator was operated at 150-200 kilos per hour in two stages. The first was a degassing stage using a pressure of $2\times10^{-1}$ mbar and a temperature of 150° C. The second stage used a pressure of $4\times10^{-2}$ mbar and a temperature of 165° C.

The properties of the resultant distillates are shown in Table 1.

TABLE 1

| No | ASA | Olefin content (%) | | | Viscosity | Polymeric | Colour |
| | | $C_{16}$ | $C_{18}$ | Total | (mPas) | residue (%) | (Gardner) |
|---|---|---|---|---|---|---|---|
| 1 | Raisafob MF (Batch A) | 0.24 | 1.92 | 2.16 | 170 | 7.24 | 6-7 |
| 2 | Raisafob MF (Batch B) | 0.78 | 3.74 | 4.52 | — | 7.52 | 4 |
| 3 | Raisafob MF (Batch C) | 0.63 | 2.48 | 3.11 | — | 7.38 | 5-6 |
| 4 | Raisafob MF (Batch D) | | | | 212 | 9.54 | 10-11 |
| 5 | Distilled Raisafob MF (Plant distillation) | 0.10 | 3.46 | 3.56 | 110 | 0.4 | 2 |
| 6 | Distilled Raisafob MF (lab distillation) | 0.16 | 0.03 | 0.19 | — | 0 | 2 |

For the plant distilled ASA the first distilled fraction (containing a significant proportion of unreacted olefin) was not discarded as it was for the laboratory distilled ASA. Therefore, although the percentage of $C_{16}$ olefin has been reduced, largely the olefin percentage of the ASA has not been affected.

2. Preparation of Emulsions of ASA and Hydrolysis Studies

Small scale emulsions for laboratory study were prepared containing 5% ASA and 0.95% Hicat 158 (cationic starch ex Roquette). Rates of hydrolysis of the resultant emulsions were measured by Fourier Transform Infra-Red spectroscopy and the results are shown in Table 2.

TABLE 2

| Temperature ° C. | ASA Remaining after 8 hours (%) | |
|---|---|---|
| | Undistilled | Distilled* |
| 30 | 81 | 90 |
| 40 | 38 | 48 |
| 50 | 0 | 4 |

*Distilled following the laboratory procedure.

The emulsion prepared with distilled ASA thus has a lower rate of hydrolysis when compared to its non-distilled counterpart.

3. Pilot Paper Machine Trial

Pilot Machine

Paper was produced on a pilot papermaking machine which had a Fourdrinier forming section with foils, table rolls, vacuum boxes, couch rolls and dandy roll. It contained an open headbox with slices.

The first press has a maximum nip pressure of 25 kg cm$^{-1}$. The second press has a plain reverse press having a maximum nip pressure of 25 kg cm$^{-1}$.

The pre-dying section includes 7 steam heated, temperature controlled cylinders with a maximum temperature of 130° C. The pilot machine was equipped with a horizontal size press. The after dryer section consisted of 3 heated cylinders with a maximum temperature of 130° C.

The pilot machine was equipped with a horizontal size press. The after dryer section consists 3 heated cylinders with a maximum temperature of 130° C. The machine calendar contained 5 nips, steam heated chilled steel rolls, with a maximum temperature of 130° C. The machine calendar contained 5 nips, steam heated chilled steel rolls, with a maximum temperature of 100° C.

The pilot machine had 1 Machine chest of 2000 litres capacity and 4 Stock holding chests of 1000 litres capacity.

The machine incorporated two tubes, separated by 1 cm, placed in the accept side of the mixing box. One tube was used for ASA emulsified with Raisamyl addition and one tube was used for starch Amylofax addition. A tube for filler addition was connected to the tube delivering dilution water to the mixing box.

Materials

| Material | Nature/Source |
|---|---|
| ASA Emulsion | ASA emulsions (1%) were prepared using a Moulinex ® type 530 food blender by emulsifying together a 1:1 ratio of ASA:Raisamyl 135 (starch). The emulsification period for all emulsions was 5 minutes. |
| ASA | Raisafob MF (undistilled) and Distilled Raisafob MF (Laboratory distillation) |
| Cationic wet end starch | Hydroxypropyltrimethylammonium ether of potato starch (available as Amylofax 75 (Avebe)) |
| Pigment | Calcium Carbonate, used as an aqueous dispersion of natural ground calcium carbonate. Weight specification 69 ± 2%. The product contained 100-200 PPM biocide and 0.15-0.5% auxiliary agent (dispersant) (available as Hydrocarb 89 ME, (Omya Croxton Garry) |
| Polyaluminium chloride solution | Pax 10% (Tan International Ltd) |
| Optical brightening agent | Tinopal ABP-Z (Ciba Speciality Chemicals PLC) |
| Pulp and water for a UK papermill. | 4 tonnes taken after the refiner<br>2 tonnes broke<br>10 tonnes of dilution water |

Machine Conditions (Reference Conditions (Wet End))

The machine was operated under the conditions set out below and also using an addition level of 0.17% ASA on paper weight. One paper (Reel No. 1A) was manufactured using the ASA emulsion produced with the ASA distillate (Laboratory scale) and the other (Reel No. 12) was manufactured with the ASA emulsion produced from Raisafob MF.

| Component | Amount |
|---|---|
| Starch | 4 kg tonne$^{-1}$ |
| PAC, to wire tray | 1 kg tonne$^{-1}$ |
| Tinopal ABP-Z-LIQ to machine chest | 5.9 litres tonne$^{-1}$ |
| pH | not adjusted |
| Water circuit | As closed as possible |

Paper

| Property | Quantity |
|---|---|
| Bulk/m$^3$ kg$^{-1}$ | 1.3 (Target 1.3) |
| Grammage/gsm | 84 (Target 80) |
| Base sheet weight/gsm | 66 (Target 66) |
| Sheet weight after filler addition | 84 (Target 80) |

4. Paper Testing from Machine Trial

The papers of Reel Nos. 1A (Invention) and 12 (Comparative) were tested (a) in the Hercules Size Test (HST) which measures the time in seconds to achieve a fixed level of penetration (i.e. high values=good sizing); and (b) for Peroxide and Lactic Acid Resistance (Raw Edge) Penetration (REP)) using the procedure described in Appendix 1.

The results were as follows:

SUMMARY AND CONCLUSIONS

Distilled ASA and paper board produced using an emulsion which comprises distilled ASA show the following advantages over their non-distilled counterparts.

1. Much better colour (Gardner of 2 compared with 4-11)
2. Much lower residual polymer content (<0.4% compared with 7-9%)
3. Much lower residual olefin content (if first fraction is discarded as the case of laboratory distillation) (<0.2% compared with 2-5%)
4. Better hydrolytic stability (10% hydrolysed in 8 hours at 30° C. compared with 20%)
5. Better Sizing performance (HST of 264 seconds compared with 167 sec)
6. Better lactic acid resistance (0.8 kg/M$^2$ after 1 hour compared with 1.1 kg/M$^2$)

7. Better Peroxide resistance (4.13 kg/m² compared with 8.41 kg/m²)

APPENDIX 1

Sizing Test Methods

Cobb and Hercules Size Test (HST)

Both Cobb and HST tests measure aqueous penetration through the XY plane.

The Cobb test measured the amount of water penetration in g/m² after exposing the XY plane to liquid water. The lower the Cobb value the lesser the penetration by water and hence the better the sizing of the paper.

The HST measures the time in seconds to achieve a fixed level of penetration. The higher the HST value the slower the penetration and hence the better the sizing of the paper.

Lactic Acid and Peroxide Resistance—Raw Edge Penetration (REP)

Sample Preparation

Samples of liquid packaging board were conditioned for 24 h at 23° C. in a humidity of 50%. The thickness of the conditioned board was measured and the sample was cut to a piece sized 10×30 cm (with the shorter side (10 cm) in the machine direction). The sample was masked on both sides cut into pieces sized 2.5×7.5 cm (with the shorter side (2.5 cm) in the machine direction), and thereafter weighed.

Lactic Acid REP

The weighed sample was placed in a basin, containing 1% lactic acid, for 24 h at room temperature. The surface was dried with absorbent boards and the sample was weighed promptly.

Peroxide REP

A lidded glass basin, containing 30% hydrogen peroxide, was heated to 70° C. The sample was placed into the basin for 10 minutes. The surface was dried with absorbent boards and weighed promptly.

REP Calculation

The REP is calculated using the following formula:

$$REP(g/mm^2)=A/a \times L$$

where

A=the weighing difference of the sample before and after treatment, g a=thickness, mm L=the perimeter of the sample, mm For each sample 5 pieces were tested.

The lower the REP value the slower the penetration and hence the better the sizing of the paper.

The invention claimed is:

1. A sized paper or board which paper or board is sized with a composition comprising an aqueous emulsion of alkenyl succinic anhydride wherein the alkenyl succinic anhydride incorporates a maximum of 0.5% by weight of polymeric residues and contains less than 0.5% by weight of olefins.

2. The sized paper or board according to claim 1, wherein the aqueous emulsion of alkenyl succinic anhydride has a lower rate of hydrolysis when compared to alkenyl succinic anhydride having 7-9% by weight polymeric residues.

3. The sized paper or board according to claim 2, further comprising a stabilizer.

4. The sized paper or board according to claim 1, wherein the paper or board is a liquid packaging board.

5. A method of producing a sized paper or board by adding to the wet-end or by size press a sizing agent which is an alkenyl succinic anhydride incorporating a maximum of 0.5% by weight of polymeric residues and less than 0.5% by weight of olefins.

6. Sized paper or board produced by the method of claim 5.

7. Sized paper or board as claimed in claim 6 provided on both surfaces thereof with a barrier coating of a food grade material.

8. A method of producing a carton comprising sterilising sized paper or board as claimed in claim 6 with hot hydrogen peroxide and converting the sterilised paper or board to a carton.

9. The method according to claim 5, wherein the alkenyl succinic anhydride incorporating a maximum of 0.5% by weight of polymeric residues is prepared by removing the polymeric residues from the alkenyl succinic anhydride.

10. The method according to claim 5, wherein the sizing agent further comprises a stabilizer.

11. The method according to claim 10, wherein the stabilizer is a starch, cationic polyacrylamide or other cationic polymer.

12. A sized paper or board comprising paper or board sized with a composition comprising an aqueous emulsion of alkenyl succinic anyhydride wherein the alkenyl succinic anhydride incorporates a maximum of 0.5% by weight of polymeric residues and contains less than 0.5% by weight of olefins and the alkenyl succinic anhydride has a lower Gardner color when compared to alkenyl succinic anhydride having 7-9% by weight polymeric residues.

13. The sized paper or board according to claim 12, wherein the lower Gardner color is a maximum of 2.

* * * * *